United States Patent
Salamone et al.

(10) Patent No.: US 7,767,794 B2
(45) Date of Patent: Aug. 3, 2010

(54) 5-FLUORO-URACIL IMMUNOASSAY

(75) Inventors: Salvatore J. Salamone, Stockton, NJ (US); Jodi Blake Courtney, Doylestown, PA (US); Dennis Stocker, Yardley, PA (US)

(73) Assignee: Saladax Biomedical Inc, Bethlehem, PA (US)

( * ) Notice: Subject to any disclaimer, the term of this patent is extended or adjusted under 35 U.S.C. 154(b) by 484 days.

(21) Appl. No.: 11/709,109

(22) Filed: Feb. 20, 2007

(65) Prior Publication Data

US 2007/0154972 A1  Jul. 5, 2007

Related U.S. Application Data

(60) Division of application No. 11/345,706, filed on Feb. 2, 2006, now Pat. No. 7,205,116, which is a continuation-in-part of application No. 11/053,480, filed on Feb. 8, 2005, now abandoned.

(51) Int. Cl.
  *C07K 16/00* (2006.01)
  *C07K 1/04* (2006.01)
(52) U.S. Cl. .......... 530/389.8; 530/388.9; 530/403

(58) Field of Classification Search .......... None
See application file for complete search history.

(56) References Cited

FOREIGN PATENT DOCUMENTS

JP  63222699  9/1988

OTHER PUBLICATIONS

Fujiwara et al. Enzyme immunoassay for the quantificaiton of mitomycin C using b-galactosidase as a label. Cancer Res. 1982, vol. 42, pp. 1487-1491.*
Yoshida et al. Clinical significance of monitoring serum levels of 5-fluorouracil by continuous infusion in patients with advanced colonic cancer. Cancer Chemother Pharmacol 1990, vol. 26, pp. 352-354.*
Nolli et al. Antibodies against antibiotics. Ann. 1st. Super. Sanita. 1991, vol. 27, No. 1, pp. 149-154.*
The Examination Report and extended European Search Report by European Patent Office, issued on Jun. 30 and Mar. 3, 2008, respectively, in the European application No. 06734206.3.

* cited by examiner

*Primary Examiner*—Shafiqul Haq

(57) ABSTRACT

Novel conjugates of 5-fluoro-uracil and novel 5-fluoro-uracil immunogens and monoclonal antibodies generated by these immunogens which are useful in immunoassays for the quantification and monitoring of 5-fluoro-uracil in biological fluids.

6 Claims, No Drawings

5-FLUORO-URACIL IMMUNOASSAY

CROSS-REFERENCE TO RELATED APPLICATION

This Application is a Divisional Application of application Ser. No. 11/345,706 filed Feb. 2, 2006 now U.S. Pat. No. 7,205,116, which is a Continuation-In-Part of application Ser. No. 11/053,480 filed Feb. 8, 2005 now abandoned.

FIELD OF THE INVENTION

This invention relates to the field of immunological assays for determining the presence and/or quantifying the amount of 5-fluoro-uracil [5-FU] in human biological samples in order to rapidly determine optimal drug concentrations during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

5-FU is one of the more commonly used cytotoxic agents that are used for the treatment of Breast and Colorectal cancer. This chemotherapeutic agent has the formula:

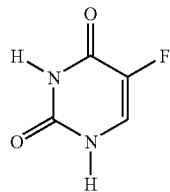

I

This compound has been associated with debilitating side effects such as bone marrow density loss, mucositis, nausea and vomiting. By monitoring the levels of 5-FU in the body and adjusting the dose these side effects can be better controlled and limited in patients.

At the same time, there is often a highly variable relationship between the dose of 5-FU and the resulting serum drug concentration that affects therapeutic effect. The degree of intra- and inter-individual pharmacokinetic variability of 5-FU can be as high as 10-fold (Diasio et. al. J. Clin. Invest. 81: pp 47-51, 1988, Wei et. al. J. Clin. Invest. 98: pp610-615, 1996) and is impacted by many factors, including:

Organ function
Genetic regulation
Disease state
Age
Drug-drug interaction
Time of drug ingestion,
Mode of drug administration, and
Technique-related administration.

As a result of this variability, equal doses of the same drug in different individuals can result in dramatically different clinical outcomes (Hon et. al. *Clinical Chemistry* 44, pp 388-400, 1998). The effectiveness of the same 5-FU dosage varies significantly based upon individual drug clearance and the ultimate serum drug concentration in the patient. Therapeutic drug management would provide the clinician with insight on patient variation in both oral and intravenous drug administrations. With therapeutic drug management, drug dosages could be individualized to the patient, and the chances of effectively treating the cancer without the unwanted side effects would be much higher (Nieto, Current Drug Metabolism 2: pp 53-66, 2001).

In addition, therapeutic drug management of 5-FU would serve as an excellent tool to ensure compliance in administering chemotherapy with the actual prescribed dosage and achievement of the effective serum concentration levels. It has been found that variability in serum concentration is not only due to physiological factors, but can also result from variation in administration technique and ability of the body to absorb 5-FU.

As a chemotherapeutic agent, 5-FU can be administered in its pro-drug form as tegafur which has the structure:

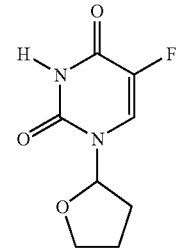

Tegafur, when administered to a patient, is generally absorbed and metabolized into 5-FU by the patient at different rates. Therefore, in monitoring the level of 5-FU in patients by means of an immunoassay, it is important that the immunoassay be able to distinguish between tegafur, the inactive substance, and 5-FU, the active substance, into which tegafur metabolizes. The problem with antibodies to 5-FU is that they could be cross-reactive with tegafur making these immunoassays not useful.

Routine therapeutic drug management of 5-FU would require the availability of simple automated tests adaptable to general laboratory equipment. Tests that best fit these criteria are immunoassays. Currently there are no immunoassays for 5-FU available and monitoring levels of this drug is conducted by physical methods like high pressure liquid chromatography (HPLC) (Escoriaza et. al. J. of Chromatography B: Biomedical Sciences and applications, 736 (1+2): pp 97-102, 1999). In order to be most effective in monitoring drug levels the antibody should be most specific to 5-FU and display very low cross-reactivity to no cross-reactivity to related pyrimidine bases, particularly tegafur.

SUMMARY OF INVENTION

In accordance with this invention, a new class of antibodies have been produced which are substantially selectively reactive to 5-FU so as to bind to 5-FU without any substantial cross reactivity to tegafur, as well as, to other interfering pyrimidine bases, uracil and cytosine. By selectively reactive it is meant that this antibody reacts with the 5-FU molecule and does not substantially react with the other interfering pyrimidine bases such as analogues of 5-FU, the most important blocking pyrimidine base being tegafur. By providing an antibody that does not substantially cross-react with tegafur, allows one to provide an immunoassay for 5-FU which can accurately monitor levels of 5-FU for therapeutic management of patients being treated with 5-FU.

It has been found that by using immunogens which are conjugates of an immunogenic polyamine polymer with a compound of the formula:

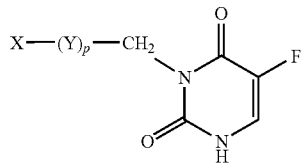

II-A wherein Y is an organic spacing group;

X is a terminal functional group capable of binding to a polyamine polymer; and p is an integer from 0 to 1.

produce antibodies which are specific for 5-FU and do not substantially react with or bind to tegafur, as well as other pyrimidine bases such as uracil, and cytosine. The provision of these antibodies which substantially selectively react with 5-FU and do not cross react with tegafur allows one to produce an immunoassay which can specifically detect and monitor 5-FU in the fluid samples of patients being treated with 5-FU. Also included within this invention are reagents and kits for said immunoassay. The presence of tegafur is the major cause for false positive readings which have made immunoassays for 5-FU unsuitable.

DETAILED DESCRIPTION

In accordance with this invention, a new class of antibodies is provided which substantially selectively reacts with 5-FU and does not substantially react or cross react with tegafur, as well as other interfering pyrimidine bases such as uracil, and cytosine. It has been discovered that through the use of the 3-substituted 5-FU derivative of formula II-A as an immunogen, this new class of antibodies of this invention are provided. It is through the use of these antibodies that an immunoassay, including reagents and kits for such immunoassay for detecting and/or quantifying 5-FU in blood, plasma or other body fluid samples has been developed. By use of this immunoassay, the presence and amount of 5-FU in body fluid samples, preferably a blood or plasma sample, can be detected and/or quantified. In this manner, a patient being treated with 5-FU can be monitored during therapy and his treatment adjusted in accordance with said monitoring. By means of this invention one achieves the therapeutic drug management of 5-FU in cancer patients being treated with 5-FU as a chemotherapeutic agent.

The reagents utilized in the immunoassay of this invention are conjugates of a carrier with the 1-substituted 5-FU compound of formula II-B:

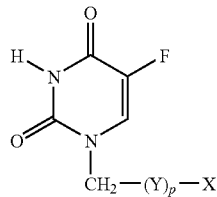

II-B wherein p, X and Y are as above;

or a compound of the formula

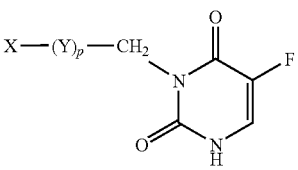

II-A wherein p, X and Y are as above;

or mixtures thereof.

In the reagents of formula II-A and II-B, the carrier can be any of the conventional reagents carriers utilized in carrying out immunoassays, preferably these carriers are labeled for detection. In the compound of formula II-A, which are utilized in forming the reagents used in the assay, X can be any functional group capable of bonding to the carrier. The preferred carriers contain a polymeric polyamine polymer with a reactive amino group and X is a terminal functional group capable of binding to a polyamine polymer.

In the immunoassay of this invention, these conjugates are competitive binding partners with the 5-FU present in the sample for the binding with the antibodies of this invention. Therefore, the amount of conjugate reagent which binds to the antibody will be inversely proportional to the amount of 5-FU in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of 5-FU in a sample is determined by correlating the measured amount of the bound or unbound conjugate produced by the 5-FU in the sample with values of the bound or unbound conjugate determined from standard or calibration curve samples containing known amounts of 5-FU, which known amounts are in the range expected for the sample to be tested. These studies for producing calibration curves are determined using the same immunoassay procedure as used for the sample.

The conjugates are prepared from compounds of formulae II-A and II-B whereas immunogens are prepared from compounds of the formula II-A. In performing the immunoassay in accordance with this invention, it is important that the conjugate be formed from the compound of formulae II-A or II-B and the immunogen be formed from the compound of formula II-A. In the conjugates including the immunogens, the polyamine polymer is conjugated with the ligand portion which has the formula:

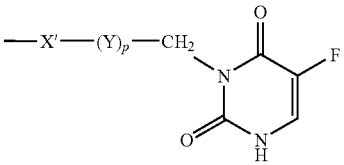

III-A wherein Y and p are as above; and x' is —CH₂— or a functional linking group;

on with the ligand portion of the compound of formula II-B which has the formula:

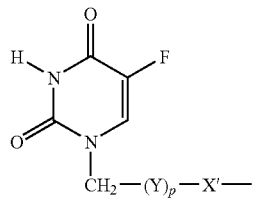

III-B wherein x', Y and p are as above.

These ligand portions may be connected in one or more active sites on the carrier of the conjugate.

Definitions

Throughout this description the following definitions are to be understood:

The terms "immunogen" and "immunogenic" refer to substances capable of eliciting, producing, or generating an immune response in an organism.

The term "conjugate" refers to any substance formed from the joining together of two parts. Representative conjugates in accordance with the present invention include those formed by the joining together of a small molecule, such as the compound of formula II-B, and a large molecule, such as a carrier or a polyamine polymer, particularly protein. In the conjugate the small molecule may be joined at one or more active sites on the large molecule.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is 5-FU.

As used herein, a "spacing group" or "spacer" refers to a portion of a chemical structure which connects two or more substructures such as haptens, carriers, immunogens, labels, or tracers through a $CH_2$ or functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein, that can join with a hapten, in this case 5-FU or the 5-FU derivatives of formula II-A described, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized.

Immunogenic carriers can also include poly amino-polysaccharides, which are a high molecular weight polymer built up by repeated condensations of monosaccharides. Examples of polysaccharides are starches, glycogen, cellulose, carbohydrate gums such as gum arabic, agar, and so forth. The polysaccharides also contain polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus*, *Staphylococcus aureus*, *E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" for forming the conjugate of formula II-B refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to the terminal functional group X in the compounds of the formula II-B.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for 5-FU. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In constructing an immunoassay, a conjugate of 5-FU is constructed to compete with the 5-FU in the sample for binding sites on the antibodies of this invention. In the immunoassay of this invention, the immunogen for producing the antibodies of this invention is the 3-substituted 5-FU derivatives of the compounds of formula III-A and the reagent is the 1-substituted 5-FU derivatives of formulae III-A or III-B. In the compounds of formula III-A and III-B, the linker spacer constitutes the —CH$_2$-(Y)$_p$-X'— portion of this molecule. The linker X' and the spacer —CH$_2$-(Y)$_p$- are conventional in preparing conjugates and immunogens. Any of the conventional spacer-linking groups utilized to prepare conjugates and immunogens for immunoassays can be utilized in the compounds of formula III-A and III-B. Such conventional linkers and spacers are disclosed in U.S. Pat. No. 5,501,987 and U.S. Pat. No. 5,101,015.

Among the preferred spacer groups are included the spacer groups hereinbefore mentioned. Particularly preferred spacing groups are groups such as alkylene containing from 1 to 10 carbon atoms,

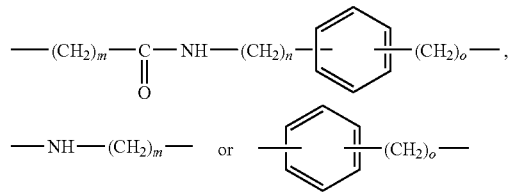

wherein n and o are integers from 0 to 6, and m is an integer from 1 to 6 with alkylene being the especially preferred spacing group. With respect to the above structures represented by Y, terminal functional group X, is connected to these substituents at their terminal end on the right side of the structures, i.e., a the end designated by (CH$_2$)$_o$ or (CH$_2$)$_m$.

In the compounds of formula III-A and III-B, X' is —CH$_2$— or a functional group linking the spacer, preferably to an amine group on the polymer or the carrier. The group X' is the result of the terminal functional group X in the compounds of Formula II-A and II-B which is capable of binding to the amino group in the polyamine polymer used as either the carrier or the immunogen. Any terminal functional group capable of reacting with an amine can be utilized as the functional group X in the compounds of formula II-A and II-B. These terminal functional groups preferably included within X are:

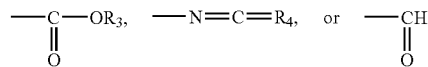

wherein R$_3$ is hydrogen or taken together with its attached oxygen atom forms a reactive ester and R$_4$ is oxygen or sulfur. The radical —N=C=R$_4$, can be an isocyanate or as isothiocyanate. The active esters formed by OR$_3$ include imidoester, such as N-hydroxysuccinamide, 1-hydroxy benzotriazole and p-nitrophenyl ester. However any active ester which can react with an amine group can be used.

The carboxylic group and the active esters are coupled to the carrier or immunogenic polymer by conventional means. The amine group on the polyamine polymer, such as a protein, produces an amide group which connects the spacer to the polymer, immunogens or carrier and/or conjugates of this invention.

In the immunogens and conjugates of the present invention, the chemical bonds between the carboxyl group-containing 5-FU hapten and the amino groups on the polyamine polymer on the carrier or the immunogen can be established using a variety of methods known to one skilled in the art. It is frequently preferable to form amide bonds. Amide bonds are formed by first activating the carboxylic acid moiety of the 5-FU hapten in the compounds of formula II-A and II-B by reacting the carboxyl group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the 5-FU hapten of formula II-A or II-B is then reacted with a buffered solution containing the protein carrier.

In cases where the 5-FU derivative of formula II-A or II-B contains a primary or secondary amino group as well as the carboxyl group, it is necessary to use an amine protecting group during the activation and coupling reactions to prevent the conjugates from reacting with themselves. Typically, the amines on the conjugate are protected by forming the corresponding N-trifluoroacetamide, N-tertbutyloxycarbonyl urethane (N-t-BOC urethane), N-carbobenzyloxy urethane or similar structure. Once the coupling reaction to the immunogenic polymer or carrier has been accomplished, as described above, the amine protecting group can be removed using reagents that do not otherwise alter the structure of the immunogen or conjugate. Such reagents and methods are known to one skilled in the art and include weak or strong aqueous or anhydrous acids, weak or strong aqueous or anhydrous bases, hydride-containing reagents such as sodium borohydride or sodium cyanoborohydride and catalytic hydrogenation. Various methods of conjugating haptens and carriers are also disclosed in U.S. Pat. No. 3,996,344 and U.S. Pat. No. 4,016,146, which are herein incorporated by reference.

On the other hand where X is a terminal isocyanate or thioisocyanate radical in the compound of formula II-A or II-B, these radicals when reacted with the free amine of a polyamine polymer produce the conjugate of formula II-B or the immunogen where X' is

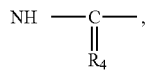

where $R_4$ is as above, which functionally connects with the carrier or the immunogenic polypeptide.

Where X, in the compounds of formula II-A and II-B, is an aldehyde group these compounds may be connected to the amine group of the polyamine polypeptide or carrier through an amine linkage by reductive amination. Any conventional method of condensing an aldehyde with an amine such as through reductive amination can be used to form this linkage. In this case, X' in the ligand portions of formula III-A and III-B is —$CH_2$—.

The 1-nitrogen atoms in the compound of formula I can be connected to form the compound of formula II-B by reacting 5-FU with a halide of the formula:

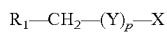

where $R_1$ is chloro or bromo and Y, p and X are as above, to produce the compound of the formula:

II-B

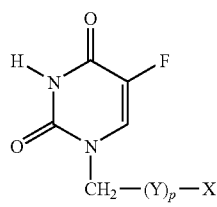

The compound of formula I is reacted at its 1-ring nitrogen atom with the halide of formula V-A to form the compounds of formula II-B by any conventional means of condensing a halide with an amine group. This condensation reaction is carried out in the presence of a base. In this reaction, the ring nitrogen atom at the 1-position of the compound of formula I is more reactive than the ring nitrogen atom at the 3-position. Therefore the ring nitrogen atom at the 1-position will preferably condense with the halide. If the compound of formula V-A contains any reactive amino or other functional substituents, these substituents can be reacted with conventional protecting groups prior to the reaction of 5-FU with a compound of V-A. After the compound of formula VI-A is produced, these protecting groups can be removed by procedures well known in the art for removing such protecting groups while retaining the amine in the compound of formula II-B.

The 3-substituted 5-FU of formula II-A can be prepared from 5-FU by first converting 5-FU into the dichloro compound of the formula:

VII

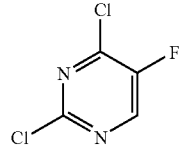

This is accomplished by treating the compound of formula I with a chlorinating agent such as phosphorous oxychloride. Any of the conditions conventional in utilizing these chlorinating agents can be used in carrying out this reaction. In the next step, the compound of formula VII is converted to the compound of the formula:

VIII-A

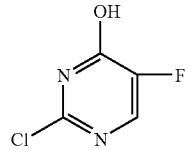

which enolizes into the compound of formula:

VIII-B

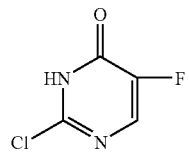

This conversion is carried out by treating the compound of formula VII with sodium hydroxide in an aqueous medium at a temperature of from 35° C. to 50° C. The compound of formula VIII-B can be converted to the compound of the formula:

IX

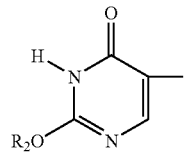

where $R_2$ is benzyl.

In forming the compound of formula IX, the compound of formula VIII-B is reacted with benzyl alcohol in an organic solvent in the presence of solid sodium hydroxide. In the next step the compound of formula IX is converted to the compound of formula II-A by reacting the compound of formula IX with the halide of formula V-A, in the manner described hereinbefore in connection with the condensation of compound of formula I with the halide of formula V-A.

The compound of formulae II-A or II-B can be converted into the conjugate carrier reagent of this invention by reacting these compounds with a polyamine, polypeptide or a carrier. The same polypeptide can be utilized as the carrier in the compound of formula II-B and as the immunogenic polymer in the immunogen of formula II-A of this invention provided that polyamine or polypeptide is immunologically active.

However, to form the conjugates, these polymers need not produce an immunological response as needed for the immunogens. In accordance with this invention, the various functional groups represented by X in the compounds of formula II-A and II-B can be conjugated to the polymeric material by conventional means of attaching a functional group to an amine group contained within the polymer. In accordance with a preferred embodiment, in the compound of formula II-A and II-B, X is a carboxylic acid group or active esters thereof.

Antibodies

The present invention also relates to novel antibodies including monoclonal antibodies to 5-FU produced by utilizing the aforementioned immunogens. In accordance with this invention it has been found that these antibodies produced in accordance with this invention are selectively reactive with 5-FU and do not react with tegafur or other pyrimidine containing compounds which would interfere with immunoassays for 5-FU.

The present invention relates to novel antibodies and monoclonal antibodies to 5-FU. The antisera of the invention can be conveniently produced by immunizing host animals with the immunogens this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals, e.g., in a preferred embodiment mice received an initial dose of 100 ug immunogen/mouse, i.p. and two or more subsequent booster shots of 100 ug immunogen/mouse over a six month period. Through periodic bleeding, the blood samples of the immunized mice were observed to develop an immune response against 5-FU binding utilizing conventional immunoassays. These methods provide a convenient way to screen for hosts which are producing antisera having the desired activity.

Monoclonal antibodies are produced conveniently by immunizing Balb/c mice according to the above schedule followed by injecting the mice with 100 ug immunogen i.p. or i.v. on three successive days starting three days prior to the cell fusion. Other protocols well known in the antibody art may of course be utilized as well. The complete immunization protocol detailed herein provided an optimum protocol for serum antibody response for the antibody to 5-FU.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In the preferred embodiment of the invention the immortal cell may be a lymphoblastoid cell or a plasmacytoma cell such as a myeloma cell, itself an antibody producing cell but also malignant. Murine hybridomas which produce 5-FU monoclonal antibodies are formed by the fusion of mouse myeloma cells and spleen cells from mice immunized against 5-FU-protein conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutageneses to produce Fab fragments or (Fab')$_2$ fragments. Single chain antibodies may be produced by joining VL and VH regions with a DNA linker (see Huston et al., *Proc. Natl. Acad. Sci. U.S.A.*, 85:5879-5883 (1988) and Bird et al., *Science*, 242:423-426 (1988))

The antibodies of this invention are selective for 5-FU and do not have any substantial cross-reactivity with such pyrimidine bases such as uracil, cytosine, tegafur etc. By having no substantial cross-reactivity it is meant that the antibodies of this invention have a cross reactivity relative to 5-FU with these metabolites of not greater than 12% preferably less than 5%.

Immunoassays

In accordance with this invention, the aforementioned conjugates and the antibodies generated from the immunogens of these compounds of formula II-A can be utilized as reagents for the determination of 5-FU in patient samples. This determination is performed by means of an immunoassay. Any immunoassay in which the reagent conjugates formed from the compounds of formula II-B compete with the 5-FU in the sample for binding sites on the antibodies generated in accordance with this invention can be utilized to determine the presence of 5-FU in a patient sample. The manner for conducting such an assay for 5-FU in a sample suspected of containing 5-FU, comprises combining an (a) aqueous medium sample, (b) an antibody to 5-FU generated in accordance with this invention and (c) the conjugates formed from the compounds of formulae II-A and II-B. The amount of 5-FU in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of 5-FU. In determining the amount of 5-FU in an unknown sample, the sample, the conjugates formed from the compounds of formula II-B and the antibody may be added in any order.

Various means can be utilized to measure the amount of conjugate formed from the compounds of formulae II-A and II-B bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. No. 4,269,511 and U.S. Pat. No. 4,420,568.

On the other hand, the antibody can be coated or absorbed on nanoparticles so that when these particles react with the 5-FU conjugates formed from the compounds of formulae II-A and II-B, these nanoparticles form an aggregate. However, when the antibody coated or absorbed nanoparticles react with the 5-FU in the sample, the 5-FU from the sample bound to these nanoparticles does not cause aggregation of the antibody nanoparticles. The amount of aggregation or agglutination can be measured in the assay mixture by absorbance.

On the other hand, these assays can be carried out by having either the antibody or the 5-FU conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compounds of formula II-B which is bound or unbound with the antibody. Other suitable labels include chromophores, fluorophores, etc.

As a matter of convenience, assay components of the present invention can be provided in a kit, a packaged combination with predetermined amounts of new reagents employed in assaying for 5-FU. These reagents include the antibody of this invention, as well as, the conjugates formed from the compounds of formulae II-A and II-B.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the examples, the following abbreviations are used for designating the following:
THF Tetrahydrofuran
EA Ethyl alcohol
DCM Dichloromethane
DMAP Dimethylaminopyridine
NHS N-hydroxy-succinimide
EDC 1-(3-dimethylaminopropyl)-3-ethylcarbodiimide hydrochloride
TLC Thin Layer Chromatrography
ANS 8-Anilino-1-naphthalenesulfonic acid
i.p. Intraperitoneal
HRP Horse radish-peroxidase
TMB 3,3',5,5'-Tetramethylbenzidine
TRIS Tris(hydroxymethyl)aminomethane hydrochloride
BSA Bovine serum albumin
BTG Bovine thyroglobulin
PBS Phosphate buffered saline
di deionized water In the examples, Scheme 1, Scheme 2, Schemes 3a, 3b and Scheme 4, below set forth the specific compounds prepared and referred to by numbers in the Examples. The schemes are as follows:

Scheme 1

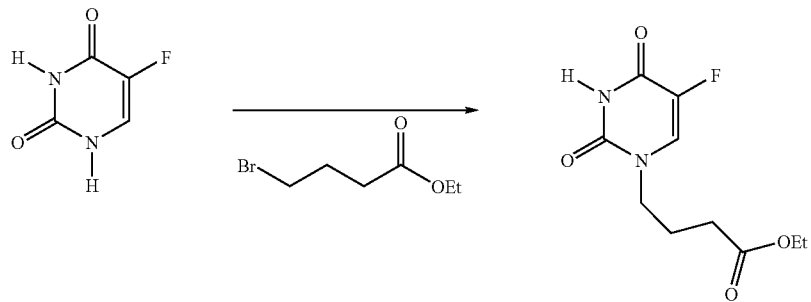

1

2

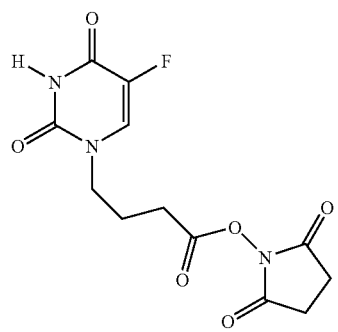

4

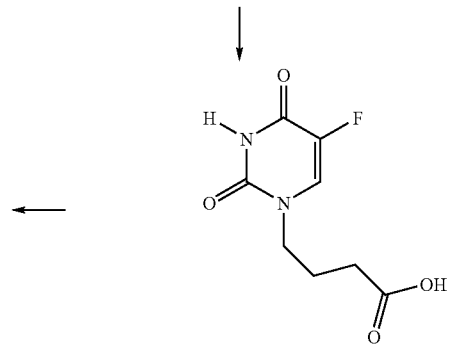

3

Scheme 2
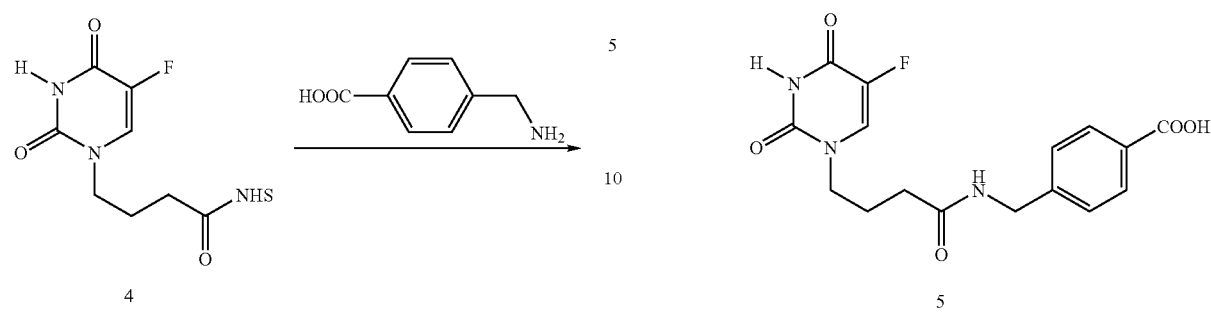
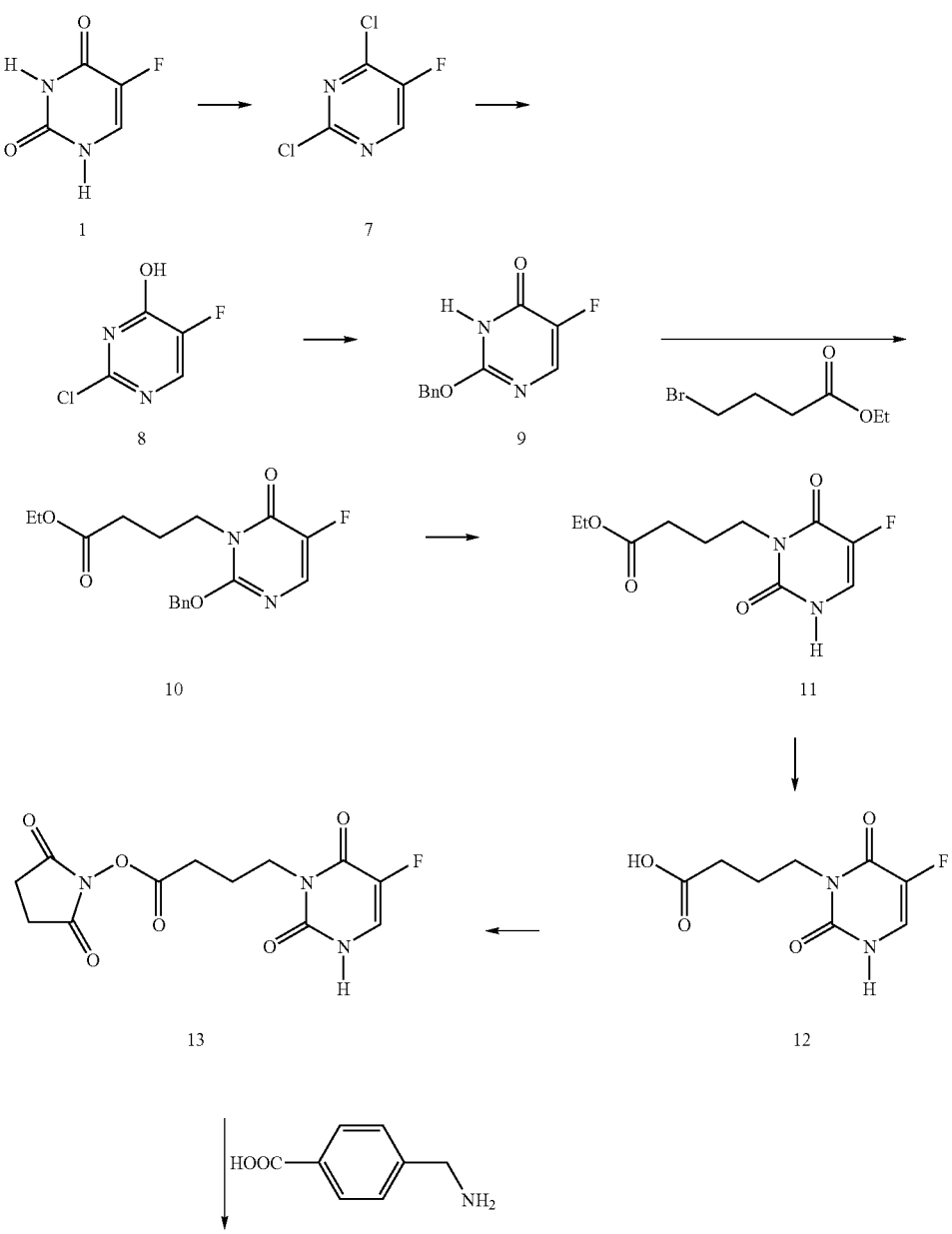

-continued

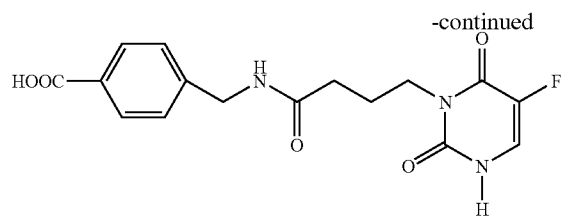

14

Scheme 3b

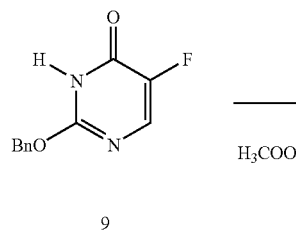 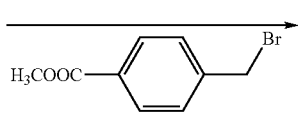

9

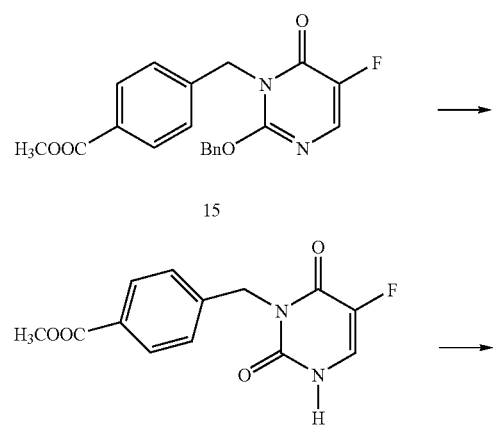

Scheme 4

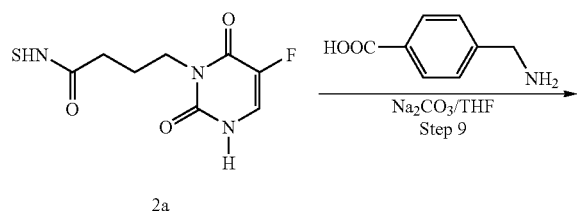

2a

-continued

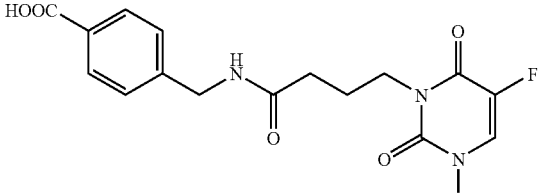

2b

EDC/NHS
Step 10

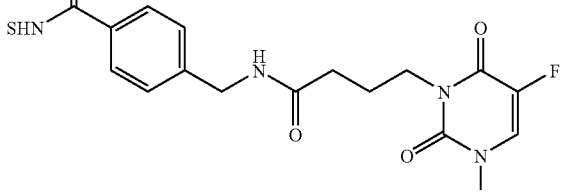

2c

Example 1

Scheme 1, Preparation of 1-substituted 5-FU Activated Ester [4]

To a solution of Fluorouracil (50 g) [1] in DMF (100 mL), triethylamine (78 g) was added at 30° C. while stirring. Then ethy-4-bromobutyrate (88.5 g) was added drop wise. After the addition was completed, the resulting reaction mixture was stirred for 48 hours at room temperature. The reaction mixture was filtered and the solvent was removed under reduced pressure. The residue was crystallized in ethyl acetate to afford 26 g (29%) of compound [2].

To a solution of [2] (20 g) in methanol (100 mL), 20% of potassium hydroxide aqueous solution (27 mL) was added. The resulting solution was stirred at room temperature for 3 hours, and then the mixture was concentrated under reduced pressure. The residue was dissolved in acetone (50-100 mL) and adjusted to pH 2~3 with concentrated HCl. It was then filtered and washed with acetone. The solid product was dissolved in acetone (50 mL) by heating. After cooling to room temperature, the solid was precipitated out by adding ethyl acetate (100 mL). The solid product was collected by filtration, followed by drying to afford about 10 g of [3]. The TLC condition for ester was ethyl acetate:ether (3:1). The TLC condition for acid is chloroform:methanol (15:1) with 2 drops of acetic acid.

To 6.3 g of compound [3] in 600 mL of dichloromethane at 0° C., NHS was added. To this a solution of DCC (4.8 g) in dichloromethane was added drop wise. After stirring for 2 hours at 0° C., the resulting reaction mixture was stirred at room temperature for 15 hours. The reaction mixture was concentrated. The residue was crystallized in acetone to give crude product. The crude product was purified on a silica gel column (eluted with ethyl acetate:ether, 3:1) to provide 4 g of compound [4].

Example 2

Scheme 2, Preparation of 1-substituted 5-FU Acid [5]

To a solution of compound [4] (3.2 g) in acetonitrile (300 mL), water (900 mL) was added, followed by addition of 1.2 eq. of p-methylamino-benzoic acid. The resulting reaction mixture was stirred at room temperature for 20 hours. The mixture was concentrated under reduced pressure to remove acetonitrile. A precipitate formed and was collected by filtration. It was then crystallized in acetone to give 2.8 g of crude product. The crude product was purified on a silica gel column (eluted with chloroform:methanol, 15:1 with 1-2 drops of acetic acid) to afford 2 g of compound [5].

Example 3a

Scheme 3a, Preparation of 3-substituted 5-FU Acid Derivatives [12], [14]

A mixture of 15.6 g of 5-FU [1] in 80 mL of $POCl_3$ was stirred in a three neck-flask equipped with condenser, thermometer and dropping funnel at 40° C. After addition of 25 mL of N,N-dimethylaniline drop wise, the resulting mixture was heated to reflux for 3 hours. The excess of $POCl_3$ was evaporated under reduced pressure. The mixture was cooled to room temperature and poured into 75 g of crushed ice. It was then extracted with chloroform (50 mL three times). The combined extracts were washed with water, dried with $MgSO_4$, and concentrated to give a yellowish solid of compound [7] in about 50% yield.

A mixture of 16 g of oxychloride [7] in 48 mL solution of 2 N NaOH was stirred at 45° C. for one hour. The pH of the reaction mixture was reduced to 7. Another 48 mL solution of 2 N NaOH was added and continued to stir until no more oily materials were observed in the reaction mixture. After the mixture was cooled to room temperature, the pH was adjusted to pH 3 with concentrated HCl. It was cooled and the product [8] precipitated out. Compound oxychloride [8] was collected and washed with water until the washing solution became neutral. The yield was about 55%.

To a three-neck flask equipped with condenser, thermometer and dean stark apparatus was added 20 mL of toluene, 52 mL of benzyl alcohol and 2.44 g of solid NaOH. The resulting mixture was refluxed until dry. Then, 3 g of Compound [8] was added and continued to be refluxed for 3 hours. After the reaction mixture was cooled to room temperature, 50 mL of water was added. The organic phase was washed with water twice (50 mL each). The aqueous phases were combined and the residues of toluene and benzyl alcohol were removed under reduced pressure. The solution was adjusted to pH 3 with concentrated HCl, cooled down, and a precipitate formed, which was collected. It was re-crystallized in ethanol to afford compound [9] in about 60% yield.

After a mixture of 20 mL of benzene, 20 mL of water and 0.5 g of tetrabutylammonium bromide was heated to 55° C., solution A (2 g of [9] in 20 mL of 1 N NaOH aqueous solution) and solution B (1.9 g of ethyl 4-bromobutyrate in 20 mL of benzene) were added into the mixture alternatively in drop wise fashion. The pH of the reaction mixture was controlled between pH 8-10. After the addition was completed, the reaction mixture was refluxed for two and a half hours. The organic phase was separated, washed with a 5% NaOH and water and dried with $MgSO_4$. The organic solvent was removed under reduced pressure. The residue was purified on a silica gel column (eluted with ether and ethyl acetate, 10:1) to give compound [10] as an oily product in about 40% yield.

A mixture of 3 g of compound [10], 0.3 g of 10% Pd/C in 50 mL of methanol was stirred under hydrogen gas (15 psi) for about 24 hours. The catalyst was removed by filtration. To the filtrate containing [10], 2 g of NaOH and 50 mL of water were added. The resulting mixture was stirred for 8 hours at room temperature. The methanol was removed under reduced pressure. The mixture was adjusted to pH 3 with concentrated HCl. After cooling, a precipitate was formed and collected by filtration. The precipitate was re-crystallized from ethanol to afford [12] in about 50% yield.

A mixture of 1 g of dried [12], 0.74 g of NHS, 1.47 g of DCC in 50 mL of chloroform was stirred for overnight (about 24 hours) at room temperature. The solvent was removed under reduced pressure and the residue was purified on a silica gel column (eluted with ethyl acetate and methanol, 10:1) to afford compound [13] in about 40% yield.

A mixture of 1 g of compound [13], 0.5 g 4-(aminomethyl) benzoic acid in 30 mL of DMF was stirred at room temperature for 8 hours. A portion of 150 mL water was added to the reaction mixture. The resulting mixture was washed with 100 mL of ethyl acetate. The aqueous phase was allowed to stand at 4° C. and the product [14] slowly precipitated out of the solution, was collected by filtration and dried under vacuum at room temperature in the presence of $P_2O_5$ to yield about 65% of [14].

Example 3b

Scheme 3b, Preparation of 3-substituted 5-FU Acid Derivative [6]

After a mixture of 20 mL of benzene, 20 mL of water and 0.5 g of tetrabutylammonium bromide was heated to 55° C., solution A (2 g of [9] in 20 mL of 1 N NaOH aqueous solution) and solution B (2.05 g of ethyl 4-bromobutyrate in 20 mL of benzene) were added into the mixture simultaneously. The pH of the reaction mixture was controlled between pH 8-10. After the addition was completed, the reaction mixture was refluxed for two and a half hours. The organic phase was separated, washed with a 5% NaOH and water and dried with $MgSO_4$. The organic solvent was removed under reduced pressure. The residue was purified on a silica gel column (eluted with ether and ethyl acetate, 10:1) to give compound [15] as an oily product in about 38% yield.

A mixture of 2 g of compound [15], 0.2 g of 10% Pd/C in 60 mL of methanol was stirred under hydrogen gas (15 psi) for about 24 hours. The catalyst was removed by filtration. The filtrate containing compound [16] was concentrated to approximately 20 mL to which was added 1 g of NaOH and 20 mL of water. The resulting mixture was stirred for 8 hours at room temperature. The methanol was removed under reduced pressure and the mixture adjusted to pH 3 with concentrated HCl. After cooling, a precipitate was formed and collected by filtration. The precipitate was re-crystallized from ethanol to afford [6] in about 60% yield.

Example 4

General Method for Preparing NHS Activated Esters from the Corresponding Acids [3,5,12,14,6]

To a stirred solution of NHS (1.39 mmol) in 20 mL of dry $CH_2Cl_2$ the acid (0.695 mmol) [3, 5, 12, 14 or 6] and EDC (2.085 mmol) were added. The solution was stirred for 18 hours at room temperature under a nitrogen atmosphere. The reaction was quenched by the addition of 3 mL of hydrochloric acid (0.3 N) and stirred for an additional 5 minutes. The organic layer was separated, dried ($Na_2SO_4$), filtered and evaporated (under vacuum) to yield a white solid.

Example 5

Preparation of 1-substituted 5-FU KLH Immunogen

To 5.86 mL of KLH (31.2 mg/mL) in 50 mM phosphate buffer (50 mM, pH 7.5) 0.692 mL of compound [4] (12.8 mg/mL in DMSO), that was prepared in Example 1, was added drop wise and the pH was adjusted to 8.5. The mixture was allowed to stir 18 hours at room temperature. This immunogenic conjugate was then purified by dialysis and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 6a

Preparation of 3-substituted 5-FU BTG Immunogen

To 11.4 mL of BTG (16.9 mg/mL) in 50 mM phosphate buffer (50 mM, pH 7.5) 1.2 mL of DMSO was added drop wise and the pH was checked to be at 7.5. To this 0.277 mL of compound [13] (52.5 mg/mL in DMSO), that was prepared in Example 3a, was added drop wise and the pH was again checked to be 7.5. The mixture was allowed to stir 18 hours at room temperature. This immunogenic conjugate was then purified by dialysis and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 6b

Preparation of 3-substituted 5-FU KLH Immunogen

To 8.3 mL of KLH (24.9 mg/mL) in 50 mM phosphate buffer (50 mM, pH 7.5) 0.922 mL of DMSO was added drop wise and the pH was checked to be at 7.5. To this 0.277 mL of compound [13] (52.6 mg/mL in DMSO), that was prepared in Example 3a, was added drop wise and the pH was again checked to be 7.5. The mixture was allowed to stir 18 hours at room temperature. This immunogenic conjugate was then purified by dialysis and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 7a

Preparation of 3-substituted 5-FU BSA Conjugate (10:1 Ratio) with Derivative 12

To a 1 mL solution of BSA (50 mg/mL) in 50 mM phosphate buffer (50 mM, pH 7.5) 0.111 mL of DMSO was added drop wise. The activated N-Hydroxysuccinimide ester of compound [12] prepared as in example 4 (0.045 mL of a 52.5 mg/mL in DMSO solution) was added drop wise. The mixture was allowed to stir overnight at room temperature to produce the conjugate of the 3-substituted 5-FU and BSA. This conjugate was then purified by dialysis and characterized according to procedures described previously (Wu et al., Bioconj. Chem., 8: pp 385-390, 1997, Li et al., Bioconj. Chem., 8: pp 896-905, 1997, Salamone et al., J. Forensic Sci. pp 821-826, 1998).

Example 7b

Preparation of 3-substituted 5-FU BSA Conjugate (1:1 Ratio) with Derivative

To 20.0 mL of BSA (50.0 mg/mL) in 50 mM phosphate buffer (50 mM, pH 7.5) 2.222 mL of DMSO was added drop wise and the pH was checked to be at 7.5. To this 0.272 mL of the activated N-Hydroxysuccinimide ester of compound [6] (20.0 mg/mL in DMSO), that was prepared in Example 4, was added drop wise and the pH was again checked to be 7.5. The mixture was allowed to stir 18 hours at room temperature. This immunogenic conjugate was then purified by dialysis and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 8

Preparation of 1-substituted 5-FU BSA Conjugate (20:1 Ratio) with Derivative 5

To a 14 mL solution of BSA (50 mg/mL) in 50 mM phosphate buffer (50 mM, pH 7.5) in an ice bath 14 mL of DMSO was added drop wise. The activated N-Hydroxysuccinimide ester of compound [5] prepared as in example 4 (1.65 mL of a 57 mg/mL in DMSO solution) was added drop wise. The mixture was allowed to stir overnight at room temperature to produce the conjugate of the 1-substituted 5-FU and BSA. This conjugate was then purified by dialysis and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 9

Preparation of 5-FU Antibodies

Ten Female BALB/c mice were immunized i.p. with 100 µg/mouse of 5-FU-KLH prepared in example 5 or with 5-FU-BTG prepared in example 6a, emulsified in Complete Freund's Adjuvant. Mice were boosted once four weeks after the initial injection with 100 µg/mouse of the same immunogens emulsified in Incomplete Freund's Adjuvant. Ten days after the boost test bleeds from each mouse were obtained by orbital bleed. The anti-serum from these test bleeds contained 5-FU antibodies evaluated in Examples 12a, 13, and 14. For monoclonal antibodies ten Female BALB/c mice were immunized i.p. with 100 μg/mouse of 3-substituted 5-FU-KLH prepared in example 6b, emulsified in Complete Freund's Adjuvant. Mice were boosted once four weeks after the initial injection with 100 μg/mouse of the same immunogens emulsified in Incomplete Freund's Adjuvant. Ten days after the boost test bleeds from each mouse were obtained by orbital bleed and these were screened as in examples 12a and 15. To produce monoclonal antibodies starting four days before the fusion (day 0), the mice were injected i.p. with 400 μg (day 3), 200 μg (day 2) and 200 μg (day 1) 3-substituted 5-FU KLH immunogen in PBS on three successive days. Spleen cells were isolated from the selected mice and fused with $2 \times 10^7$ SP2/0 cells with 50% polyethylene glycol 1500 according to the method of Coligan, J. E. et al., eds., *Current Protocols in Immunology*, 2.5.1-2.5.8, (1992), Wiley & Sons, NY. The fused cells were plated on 10 96-well plates in DMEM/F12 supplemented with 20% FetalClone I, 2% L-glutamine (100 mM) and 2% 50×HAT. Two weeks later, the hybridoma supernatant was assayed for the presence of anti-5-FU by ELISA (example 12b). Positive wells were expanded and again screened by the same method. The positive clones were confirmed for 5-FU binding by a competitive ELISA (examples 12a and 15). Clones positive by ELISA were subcloned once or twice by limiting dilution according to the method disclosed in Coligan, J. E. et al., eds., *Current Protocols in Immunology*, 2.5.8-2.5.17, (1992), Wiley & Sons, NY.

Example 10

Microtiter Plate Sensitization Procedure with 5-FU Derivative 5—BSA Conjugate

The ELISA method for measuring 5-FU concentrations was performed in polystyrene microtiter plates (Nunc MaxiSorp C8 or F8 Immunomodules) optimized for protein binding and containing 96 wells per plate. Each well was coated with 5-FU-BSA conjugate (prepared as in example 8) by adding 300 μL of 5-FU-BSA conjugate at 10 μg/mL in 0.05M sodium bicarbonate, pH=9.6, and incubating for three hours at room temperature. The wells were washed with 0.05M sodium bicarbonate, pH 9.6 and then were blocked with 400 μL of 5% sucrose, 0.2% sodium caseinate solution for 30 minutes at room temperature. After removal of the post-coat solution the plates were dried at 37° C. overnight.

Example 11a

Microtiter Plate Sensitization Procedure with 5-FU Derivative 12—BSA Conjugate

The ELISA method for measuring 5-FU concentrations was performed in polystyrene microtiter plates (Nunc MaxiSorp C8 or F8 Immunomodules) optimized for protein binding and containing 96 wells per plate. Each well was coated with 5-FU-BSA conjugate (prepared as in example 7a) by adding 300 μL of 5-FU-BSA conjugate at 10 μg/mL in 0.05M sodium bicarbonate, pH=9.6, and incubating for three hours at room temperature. The wells were washed with 0.05M sodium bicarbonate, pH 9.6 and then were blocked with 400 μL of 5% sucrose, 0.2% sodium caseinate solution for 30 minutes at room temperature. After removal of the post-coat solution the plates were dried at 37° C. overnight.

Example 11b

Microtiter Plate Sensitization Procedure with 5-FU Derivative 6—BSA Conjugate

The ELISA method for measuring 5-FU concentrations was performed in polystyrene microtiter plates (Nunc MaxiSorp C8 or F8 Immunomodules) optimized for protein binding and containing 96 wells per plate. Each well was coated with 5-FU-BSA conjugate (prepared as in example 7b) by adding 300 μL of 5-FU-BSA conjugate at 10 μg/mL in 0.05M sodium bicarbonate, pH=9.6, and incubating for three hours at room temperature. The wells were washed with 0.05M sodium bicarbonate, pH 9.6 and then were blocked with 375 μL of 5% sucrose, 0.2% sodium caseinate solution for 30 minutes at room temperature. After removal of the post-coat solution the plates were dried at 37° C. overnight.

Example 12a

Antibody Screening Procedure—Titer

The ELISA method for screening 5-FU antibodies (produced in example 9) was performed with the microtiter plates that were sensitized with 5-FU-BSA as described in examples 7a, 7b and 8. The antibody screening assay was performed by diluting the antisera containing 5-FU antibodies to 1:100, 1:1,000, 1:10,000 and 1:100,000 in phosphate buffered saline containing 0.1% BSA and 0.01% thimerosal. To each well of 5-FU-BSA sensitized wells (prepared in examples 11a, 11b and 10) 100 μL of diluted antibody was added and incubated for 10 minutes at room temperature with shaking. During this incubation antibody binds to the 5-FU-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of 5-FU antibody bound to the 5-FU-BSA conjugate in the wells, 100 μL of a goat anti-mouse antibody—HRP enzyme conjugate (Jackson Immunoresearch) diluted 1/2000 in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to 5-FU antibodies in the wells, the plates were again washed three times to remove unbound goat anti-mouse antibody—HRP enzyme conjugate. To develop a measurable color in the wells washing was followed by the addition of 100 μL of TMB (TMB Liquid Substrate, Sigma or BioFx), a substrate for HRP, to develop color during a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and was expressed as the dilution (titer) resulting in an absorbance of 1.5. Titers were determined by graphing log antibody dilution of the antibody measured (x-axis) vs. absorbance 650 nm (y-axis) and extrapolating the titer at an absorbance of 1.5. The titer determined the concentration (dilution) of antibody used in the indirect competitive Microtiter plate assay described in examples 13, 14 and 15.

Example 12b

Antibody Screening Procedure—Monoclonal Screening

The ELISA method for screening 5-FU monoclonal antibodies (produced in example 9) was performed with the microtiter plates that were sensitized with 5-FU-BSA as described in example 7b. To each well of 5-FU-BSA sensitized wells (prepared in example 11b) 50 uL phosphate buffered saline containing 0.1% BSA and 0.01% thimerosal and then 50 µL of monoclonal culture supernatant were added and incubated for 10 minutes at room temperature with shaking. During this incubation antibody binds to the 5-FU-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of 5-FU antibody bound to the 5-FU-BSA conjugate in the wells, 100 µL of a goat anti-mouse antibody—HRP enzyme conjugate (Jackson Immunoresearch) diluted to a predetermined specific activity (approximately 1/2000) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to 5-FU antibodies in the wells, the plates were again washed three times to remove unbound goat anti-mouse antibody—HRP enzyme conjugate. To develop a measurable color in the wells washing was followed by the addition of 100 µL of TMB (TMB Liquid Substrate, Sigma or BioFx), a substrate for HRP, to develop color during a 10 minute incubation with shaking at room temperature.

Following the incubation for color development, 50 µL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured. Samples with an absorbance of greater than twice background were designated as positive.

Example 13

Indirect Competitive Microtiter Plate Immunoassay Procedure Determining IC50 and Cross-Reactivity for Antibodies to 5-fU Derivative 4 Conjugate The ELISA method for measuring 5-FU concentrations was performed with the microtiter plates that were sensitized with 5-FU-BSA described in example 7a. 5-FU, uracil, thymine, cytosine and Tegafur were diluted 10 fold in PBS over a concentration range of 0.01 to 10,000 ng/mL. The assay was performed by incubating 50 µL of the analytes to be measured with 50 µL of antibody (produced in example 9 with immunogen of example 5) diluted to a titer determined in example 12a. During the 10 minute incubation (R.T., with shaking) there is a competition of antibody binding for the 5-FU conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of 5-FU antibody bound to the 5-FU-BSA conjugate in the wells, 100 µL of a goat anti-mouse antibody—HRP enzyme conjugate (Jackson Immunoresearch) diluted 1/2000 in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to 5-FU antibodies in the wells, the plates were again washed three times to remove unbound secondary conjugate. To develop a measurable color in the wells washing was followed by the addition of 100 µL of TMB (TMB Liquid Substrate, Sigma or BioFx), a substrate for HRP, to develop color in a 10 minute incubation with shaking at room temperature. Following the incubation for color development, 50 µL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and inversely proportional to the amount of 5-FU in the sample. The absorbance of the color in the wells containing analyte was compared to that with no analyte and a standard curve was generated. The IC50 value for a given analyte was defined as the concentration of analyte that is required to inhibit 50% of the absorbance for the wells containing no analyte. The cross-reactivity of a given analyte was calculated as the ratio of the IC50 for 5-FU to the IC50 for uracil, thymine, cytosine and Tegafur expressed as a percent. When measured with an antibody as produced in example 9 with immunogen of example 5 the percent cross-reactivities relative to 5-FU for uracil, thymine, and cytosine were less than 7% and 200% for tegafur. The results are in table I.

Example 14

Indirect Competitive Microtiter Plate Immunoassay Procedure Determining IC50 and Cross-Reactivity for Antibodies to 5-FU Derivative 13 Conjugate The ELISA method for measuring 5-FU concentrations was performed with the microtiter plates that were sensitized with 5-FU-BSA described in example 8. 5-FU, uracil, thymine, cytosine and Tegafur were diluted 10 fold in PBS over a concentration range of 0.01 to 10,000 ng/mL. The assay was performed by incubating 50 µL of the analytes to be measured with 50 µL of antibody (produced in example 9) diluted to a titer determined in example 12a. During the 10 minute incubation (R.T., with shaking) there is a competition of antibody binding for the 5-FU conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of 5-FU antibody bound to the 5-FU-BSA conjugate in the wells, 100 µL of a goat anti-mouse antibody—HRP enzyme conjugate (Jackson Immunoresearch) diluted 1/2000 in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to 5-FU antibodies in the wells, the plates were again washed three times to remove unbound secondary conjugate. To develop a measurable color in the wells washing was followed by the addition of 100 µL of TMB (TMB Liquid Substrate, Sigma or BioFx), a substrate for HRP, to develop color in a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and inversely proportional to the amount of 5-FU in the sample. The absorbance of the color in the wells containing analyte was compared to that with no analyte and a standard curve was generated. The IC50 value for a given analyte was defined as the concentration of analyte that is required to inhibit 50% of the absorbance for the wells containing no analyte. The cross-reactivity of a given analyte was calculated as the ratio of the IC50 for 5-FU to the IC50 for uracil, thymine, cytosine and Tegafur expressed as a percent. When measured with an antibody as produced in example 9 with immunogen of example 6a the percent cross-reactivates relative to 5-FU for uracil was less than 8%, for cytosine less than 0.03%, less than 1% for tegafur and about 12% for thymine. The results are in table I.

Example 15

Indirect Competitive Microtiter Plate Immunoassay Procedure Determining IC50 and Cross-Reactivity for Antibodies to 5-FU Derivative 13 Conjugate The ELISA method for measuring 5-FU concentrations was performed with the microtiter plates that were sensitized with 5-FU-BSA described in example 7b. 5-FU, uracil, thymine, cytosine and Tegafur were diluted 10 fold in PBS over a concentration range of 0.1 to 1,000,000 ng/mL depending on the sample. The assay was performed by incubating 50 μL of the analytes to be measured with 50 μL of antibody (produced in example 9) diluted to a titer determined in example 12a. During the 10 minute incubation (R.T., with shaking) there is a competition of antibody binding for the 5-FU conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of 5-FU antibody bound to the 5-FU-BSA conjugate in the wells, 100 μL of a goat anti-mouse antibody— HRP enzyme conjugate (Jackson Immunoresearch) diluted to a predetermined specific activity (approximately 1/2000) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to 5-FU antibodies in the wells, the plates were again washed three times to remove unbound secondary conjugate. To develop a measurable color in the wells washing was followed by the addition of 100 μL of TMB (TMB Liquid Substrate, Sigma or BioFx), a substrate for HRP, to develop color in a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and inversely proportional to the amount of 5-FU in the sample. The absorbance of the color in the wells containing analyte was compared to that with no analyte and a standard curve was generated. The IC50 value for a given analyte was defined as the concentration of analyte that is required to inhibit 50% of the absorbance for the wells containing no analyte. The cross-reactivity of a given analyte was calculated as the ratio of the IC50 for 5-FU to the IC50 for uracil, thymine, cytosine and Tegafur expressed as a percent. When measured with a monoclonal antibody as produced in example 9 with immunogen of example 6b the percent cross-reactivities relative to 5-FU for uracil was less than 8%, less than 0.01% for cytosine, about 1% for tegafur and less than 4% for thymine. The results are in table II.

TABLE 1

Cross-Reactivity of 5-Fluorouracil Immunoassays with Related Compounds
Using polyclonal antibodies

| Immunoassay Systems | | | | | | |
|---|---|---|---|---|---|---|
| | Plate Coating | Cross-Reactivity | | | | |
| Immunogen | Conjugate | 5Fluorouracil | Uracil | Thymine | Cytosine | Tegafur |
| 1-Substituted KLH Immunogen (Scheme 1, Cmpd 4, Example 5) Compound II-B | 3-Substituted BSA Conjugate (10:1 ratio) (Scheme 3a, Cmpd 12, Example 7a) Compound II-A | 100.0% | 4.0% | 6.7% | <0.1% | 200.0% |
| 3-Substituted BTG Immunogen (Scheme 3a, Cmpd 12, Example 6a) Compound II-A | 1-Substituted BSA Conjugate (20:1 ratio) (Scheme 2, Cmpd 5, Example 8) Compound II-B | 100.0% | 7.5% | 12.0% | <0.3% | 0.5% |

TABLE 2

Cross-Reactivity of 5-Fluorouracil Immunoassay using a monoclonal antibody to 3-substituted-KLH (example 6b) with plate coating 3-substitued-5-FU compound-BSA conjugate (example 7b).

| Immunoassay Systems | | Cross-Reactivity | | | | |
|---|---|---|---|---|---|---|
| Immunogen | Plate Coating Conjugate | 5Fluorouracil | Uracil | Thymine | Cytosine | Tegafur |
| 3-Substituted KLH Immunogen (Scheme 3a, Cmpd 12, Example 6b) Compound II-A | 3-Substituted BSA Conjugate (Scheme 3b, Cmpd 6, Example 7b) Compound II-A | 100.0% | 7.3% | 3.2% | <0.01% | 1.0% |

The results in these tables demonstrate the importance of forming the immunogen from the compound of formula II-A and the reagent from the compound of formula II-A or II-B. From these results it can be seen that it is when the immunogen is formed from the compound of formula II-A, rather than II-B, an antibody is produced which does not cross-react with Tegafur. It is through the antibody provided from the immunogen of the compound of the formula II-A and the reagent carrier provided from the compound of II-A or II-B, that produces an accurate immunoassay for 5-FU to monitor patients being treated with 5-FU.

What is claimed:

1. An antibody which binds selectively to 5-fluoro-uracil and has a cross-reactivity with each of uracil, cytosine and tegafur of not greater than 12%, said cross reactivity being relative to its binding to 5-fluoro-uracil.

2. The antibody of claim 1, wherein said antibody is a monoclonal antibody.

3. The antibody of claim 2, wherein said antibody is derived from mice, rabbits or rats.

4. The antibody of claim 1, wherein said antibody is derived from an immunogenic carrier containing a polyamine polymer conjugated to a compound of the formula:

II-A

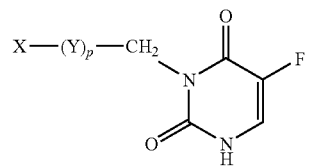

wherein Y is an organic spacing group;
X is a terminal functional group capable of binding to a polyamine polymer; and
p is an integer from 0 to 1.

5. The antibody of claim 4, wherein said antibody is a monoclonal antibody.

6. The antibody of claim 5, wherein said antibody is derived from mice, rabbits or rats.

* * * * *